(12) United States Patent
Dunham et al.

(10) Patent No.: US 7,027,553 B2
(45) Date of Patent: Apr. 11, 2006

(54) SYSTEMS AND METHODS FOR GENERATING IMAGES BY USING MONOCHROMATIC X-RAYS

(75) Inventors: Bruce Matthew Dunham, Mequon, WI (US); John Scott Price, Wauwatosa, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 206 days.

(21) Appl. No.: 10/747,510

(22) Filed: Dec. 29, 2003

(65) Prior Publication Data

US 2005/0147199 A1  Jul. 7, 2005

(51) Int. Cl.
*A61B 6/03* (2006.01)

(52) U.S. Cl. .............................. 378/5; 378/119; 378/62
(58) Field of Classification Search .................. 378/62, 378/4, 119, 5, 16
See application file for complete search history.

(56) References Cited

U.S. PATENT DOCUMENTS

| | | | |
|---|---|---|---|
| 4,598,415 A * | 7/1986 | Luccio et al. ................ | 378/119 |
| 4,688,227 A | 8/1987 | Chan et al. | |
| 4,726,046 A | 2/1988 | Nunan | |
| 4,975,917 A | 12/1990 | Villa | |
| 5,227,733 A | 7/1993 | Yamada | |
| 5,353,291 A | 10/1994 | Sprangle et al. | |
| 5,495,515 A | 2/1996 | Imasaki | |
| 5,815,517 A | 9/1998 | Ikegami | |
| 5,825,847 A | 10/1998 | Ruth et al. | |
| 5,887,008 A | 3/1999 | Ikegami | |
| 6,035,015 A | 3/2000 | Ruth et al. | |
| 6,101,234 A * | 8/2000 | Ali et al. ........................ | 378/4 |
| 6,226,354 B1 * | 5/2001 | Mamine ..................... | 378/119 |
| 6,332,017 B1 * | 12/2001 | Carroll et al. ............. | 378/119 |
| 2003/0048868 A1 | 3/2003 | Bailey et al. | |

OTHER PUBLICATIONS

M. Bertolotti and C. Sibilia. Coherent gamma radiation production by interaction between a relativistic electron beam and two interfereing laser fields; May 18, 1982; The American Physical Society; vol. 26, No. ; p. 3187.*

Sprangle, P. Tunable, Short Pulse Hard X-rays from a Compact Laser Synchrotron Source, J. Appl. Phys. 72 (11) Dec. 1, 1992, 1992 American Institute of Physics, pp. 5032-5038.

* cited by examiner

*Primary Examiner*—Edward J. Glick
*Assistant Examiner*—Mona Sanei
(74) *Attorney, Agent, or Firm*—Carl B. Horton, Esq.; Armstrong Teasdale. LLP

(57) ABSTRACT

A system for generating images by using monochromatic x-rays is described. The system includes an accelerator configured to increase energy of an electron beam, at least one detector element configured to receive x-rays having multiple energies generated by interaction of the electron beam with at least one laser beam, and an image reconstructor configured to reconstruct at least one image by processing the x-rays.

19 Claims, 3 Drawing Sheets

SYSTEMS AND METHODS FOR GENERATING IMAGES BY USING MONOCHROMATIC X-RAYS

BACKGROUND OF THE INVENTION

This invention relates generally to imaging systems and more particularly to systems and methods for generating images by using monochromatic x-rays.

In radiotherapy, as practiced in x-ray oncology, an amount of radiation, or dose is delivered to a defined, predetermined region of a patient's body. Because high levels of high energy radiation are used during radiation therapy treatment, it is important that a therapist be able to locate a site to be treated. Before a high-energy treatment machine is used to actually deliver the radiation for treatment, a low-energy imaging machine is used preliminarily to determine exactly where the dose should be delivered. For example, radiation therapists often attempt to use scans from diagnostic computed tomography (CT) scanners in planning a radiation therapy treatment. However, the CT scanners are separate from the high-energy treatment machine used for radiation therapy treatment, and therefore consume additional space and result in an additional cost.

BRIEF DESCRIPTION OF THE INVENTION

In one aspect, a system for generating images by using monochromatic x-rays is provided. The system includes an accelerator configured to increase energy of an electron beam, at least one detector element configured to receive x-rays having multiple energies generated by interaction of the electron beam with at least one laser beam, and an image reconstructor configured to reconstruct at least one image by processing the x-rays.

In another aspect, a system for generating images by using monochromatic x-rays is provided. The system includes an accelerator configured to accelerate an electron beam received from a gun, and at least one detector element configured to receive x-rays generated by interaction of the electron beam with at least two laser beams, where one of the at least two laser beams has a different wavelength than a wavelength of remaining of the at least two laser beams, and an image reconstructor configured to reconstruct at least one image by processing the x-rays.

In yet another aspect, a method for generating images by using monochromatic x-rays is described. The method includes accelerating an electron beam, generating x-rays having multiple energies by interaction of the electron beam with at least one laser beam, and reconstructing at least one image by processing the x-rays.

DETAILED DESCRIPTION OF THE INVENTION

As used herein, an element or step recited in the singular and preceded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate or are configured to generate at least one viewable image.

Figure 1:
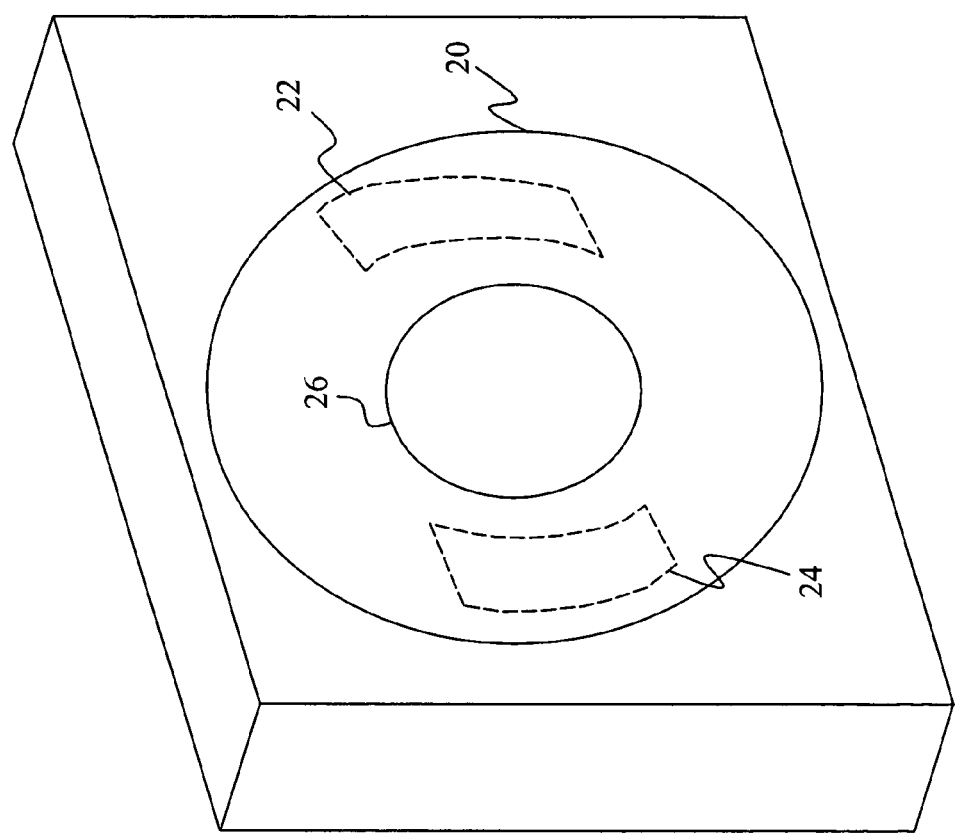
FIG. 1 is an isometric view of an embodiment of an embodiment of a gantry.

FIG. 1 is an isometric view of an embodiment of an embodiment of a gantry 20. An inverse Compton scatter source 22, and a detector array 24 including one or more detector elements, are located within gantry 20. In one embodiment, detector array 24 is a non-energy discriminating array that does not distinguish between multiple energies. In an alternative embodiment, detector array 24 is an energy discriminating array that distinguishes between multiple energies. Gantry 20 has an opening 26 in which a subject, such as a patient or a phantom, is placed.

Source 22 projects a fan-shaped x-ray beam, which is collimated to lie within an X-Y plane, referred to as an "imaging plane", of a Cartesian coordinate system. As an example, the x-ray beam emitted from source 22 is a monochromatic x-ray beam having an energy ranging from 10–200 kilo electron volts (keV). As another example, the x-ray beam has an energy of 10 mega electron volts (MeV).

The x-ray beam passes through the subject being imaged to generate an attenuated radiation beam. The attenuated radiation beam impinges upon detector array 24. Intensity of the attenuated radiation beam received at detector array 24 is dependent upon the attenuation of the x-ray beam by the subject. Each detector element of detector array 24 produces a separate electrical signal that is a measurement of the attenuation by detector array 24. The attenuation measurements from all the detector elements are acquired separately to produce a transmission profile. Source 22 and detector array 24 rotate with gantry 20 around the subject to be imaged such that an angle at which the x-ray beam intersects the subject constantly changes. A group of x-ray attenuation measurements, i.e., projection data, from detector array 24 at one gantry angle is referred to as a "view". A "scan" of the subject includes a set of views made at different gantry angles during one revolution of source 22 and detector array 24. Gantry 20 rotates around subject to scan the subject from different directions to obtain a variety of views of the subject.

Figure 2:
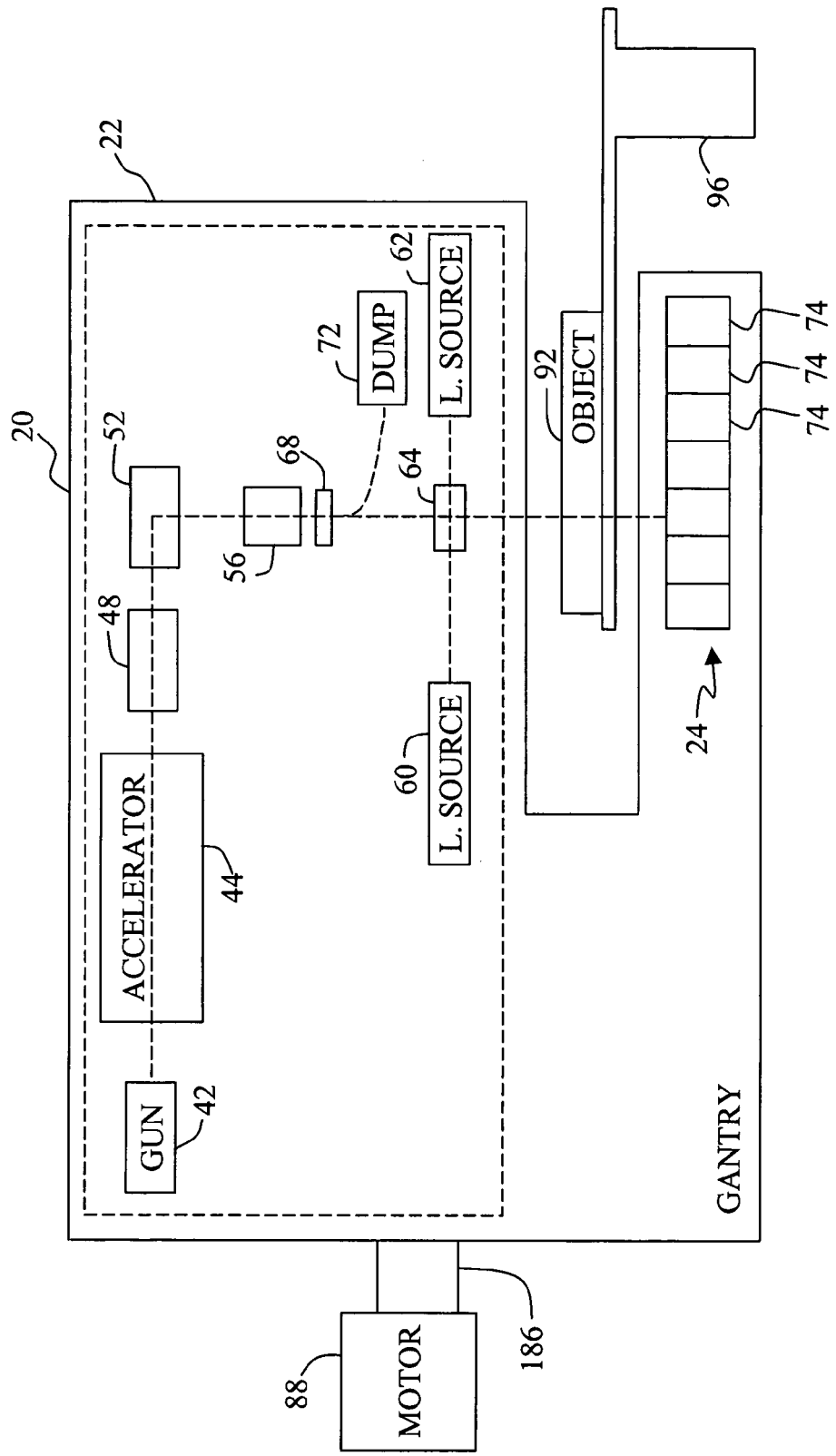
FIG. 2 is a side view of the gantry of FIG. 1.

FIG. 2 is a side view of gantry 20. A gun 42, a linear accelerator 44, a focusing device 48, an achromatic magnet 52, a collimator 56, laser sources 60 and 62, a mirror 64, an ion chamber 68, an electron dump 72, and detector array 24 including one or more detector elements 74, are located within gantry 20. In an alternative embodiment, one laser source or more than two laser sources can be used within gantry 20. Detector array 24 includes a row of detector elements 74. In an alternative embodiment, detector array 24 includes multiple rows of detector elements 74, where each row is parallel to every other row of detector elements 74. An example of gun 42 is a gun that operates at a high voltage, for instance, between 70–90 kilovolts (kV), and generates electron beams. Another example of gun 42 is a radio frequency (RF) gun. An example of focusing device 48 is a quadrupole triplet. An example of collimator 56 is a collimator made from lead or tungsten, and having a square-shaped aperture. An example of achromatic magnet 52 is a magnet having a first sector that bends a beam, received by achromatic magnet 52, by 45 degrees clockwise, and having a second sector that further bends the beam by 45 degrees clockwise so that a total bending of 90 degrees is achieved. As another example, achromatic magnet 52 includes six sectors, each of which bends the beam by 45 degrees counterclockwise to achieve a total bending of 270 degrees counterclockwise. In an alternative embodiment, achromatic magnet 52, accelerator 44, and gun 42 are placed parallel to a vertical axis passing through a center of gantry 20 because there is no need to bend the electron beam generated from gun 42 to direct the electron beam toward mirror 64.

Gun 42 generates the electron beam and accelerator 44 increases a speed of the electron beam to generate an accelerated beam. Accelerator 44 increases the speed of the electron beam by increasing energy of the electron beam. As an example, the electron beam generated by gun 42 has an energy ranging from 10–100 MeV. The accelerated beam transits via focusing device 48 that focuses the accelerated beam to generate a focused accelerated beam. Achromatic magnet 52 bends the focused accelerated beam to lie in a plane parallel to the vertical axis of gantry 20, thereby generating a bent beam. Collimator 56 absorbs scattered electrons of the bent beam to generate a collimated beam.

Ion chamber 68 is mounted at the bottom of collimator 56, travels with collimator 56, and monitors dose rate, measured in radians/time, of the collimated beam. The dose rate measured by ion chamber 68 may be compared with a dose rate of the attenuated radiation beam received by detector array 24. Laser source 60 generates a first laser beam that is directed toward mirror 64. As an example, wavelength of the first laser beam generated from laser source 60 ranges from ultraviolet to infrared range. Both laser source 60 and gun 42 are pulsed. Pulses within the electron beam generated by gun 42 and within the first laser beam are synchronized to increase efficiency, and to reduce background radiation. In one embodiment, the synchronization can be achieved by triggering gun 42 with the first laser beam generated by laser source 60.

Mirror 64 is placed at an angle ranging between, for example, 30 and 60 degrees, with respect to an axis that is perpendicular to the vertical axis of gantry 20 to target the first laser beam towards the collimated beam. When electrons of the collimated beam interact with photons of the first laser beam, inverse Compton scattering occurs. Inverse Compton scattering is described in detail in P. Sprangle, A. Ting, E. Esarey, and A. Fisher, Tunable, Short Pulse Hard X-rays From A Compact Laser Syncrottron Source, J. Appl. Phys., Vol. 72, No. 11, 5032–5038 (1992). In inverse Compton scattering, an electron of a beam loses energy to a photon of a laser beam when the electron interacts with the photon. After the collimated beam interacts with the first laser beam, a first x-ray beam is generated. The first x-ray beam follows a path which is approximately collinear with the collimated beam. As an example, the first x-ray beam is a monochromatic x-ray beam having energies ranging from 10–200 keV. The energy of the first x-ray beam is manipulated by changing the energy of the electron beam, or by changing the wavelength of the first laser beam. As an example, if energy of the electron beam is 72 MeV and wavelength of the first laser beam is 1 micron, energy of the first x-ray beam is 100 keV. As another example, if energy of the electron beam is 25 MeV, for wavelengths of 1.06 micron, 0.532 micron, and 0.266 micron of the first laser beam, respective energies of the first x-ray beam are approximately 12 keV, 24 keV, and 48 keV. A residual portion of the collimated beam remaining after the collision between the collimated beam and the first laser beam is deflected by a magnet (not shown) into electron dump 72.

In an alternative embodiment, laser source 62 generates a second laser beam. As an example, wavelength of the second laser beam generated from laser source 60 ranges from ultraviolet to infrared range. Wavelength of the second laser beam is different than wavelength of the first laser beam. In an alternative embodiment, wavelength of the second laser beam is the same as that of the first laser beam. Both laser source 62 and gun 42 are pulsed. Pulses within the electron beam generated by gun 42 and within the second laser beam are synchronized to increase efficiency, and to reduce background radiation. In one embodiment, the synchronization can be achieved by triggering gun 42 with the second laser beam generated by laser source 62.

Mirror 64 is placed at an angle ranging between, for example, 30 and 60 degrees, with respect to an axis that is perpendicular to the vertical axis of gantry 20 to target the second laser beam towards the collimated beam. When electrons of the collimated beam interact with photons of the second laser beam, inverse Compton scattering occurs. After the collimated beam interacts with the second laser beam, a second x-ray beam is generated. The second x-ray beam follows a path which is approximately collinear with the collimated beam and has an energy that is different than energy of the first x-ray beam. In an alternative embodiment, energy of the second x-ray beam is the same as the energy of the first x-ray beam. As an example, the second x-ray beam is a monochromatic x-ray beam having energies ranging from 10–200 keV. The energy of the second x-ray beam is manipulated by changing the energy of the electron beam, or by changing the wavelength of the second laser beam. A residual portion of the collimated beam remaining after the collision between the collimated beam and the second laser beam is deflected by a magnet (not shown) into electron dump 72.

The first and the second laser beams are generated simultaneously or consecutively to interact with the collimated beam. In an alternative embodiment, more than two laser beams are generated to simultaneously or consecutively interact with the collimated beam. For example, a third laser beam can be generated by one of laser sources 60 and 62 or by another laser source (not shown) to interact with the collimated beam. When the first and the second laser beams are generated consecutively, the first laser beam is generated before the second laser beam is generated or the second laser beam is generated before the first laser beam is generated. In one embodiment, the first and the second laser beams can be consecutively generated by any one of laser sources 60 and 62. When the first and the second laser beams are generated simultaneously and interact with the collimated beam, an x-ray spectra with two or more monochromatic peaks is produced.

It is noted that any one of the first and second laser beams can impinge on the collimated beam from an angle ranging from 0 to 90 degrees. As the angle increases, it becomes more convenient to package gun 42, accelerator 44, and laser sources 60 and 62. As the angle decreases, efficiency of production of one of the first and second beams increases.

Gantry 20 is rotated around a center of rotation of gantry 20 while an x-ray beam resulting from the simultaneous or consecutive generation of the first and second laser beams, is emitted toward the subject. Gantry 20 is rotated via a shaft 86 coupled to a motor 88. Detector array 24 and source 22 rotate with gantry 20. Gantry 20 rotates at a slow speed, such as, for example, ranging from approximately 1 rotation per second to 1 rotation per minute. Due to the slow speed of rotation, there is correction of any errors resulting from motion of the subject during the rotation.

The x-ray beam is intercepted and attenuated by an object 92, such as cancerous tissues, lungs, heart, liver, or kidneys, of the subject to generate the attenuated radiation beam. Object 92 lies on a table 96, such as a motorized table, which is capable of moving in various directions, such as, for example, in a direction perpendicular to the vertical axis of gantry 20.

Detector elements 74 of detector array 24 receive the attenuated radiation beam and generate electrical signals that are attenuation measurements of intensities of the attenuated radiation beam. The attenuation measurements are processed by a system, shown in FIG. 3, for generating images by using monochromatic x-rays.

Figure 3:
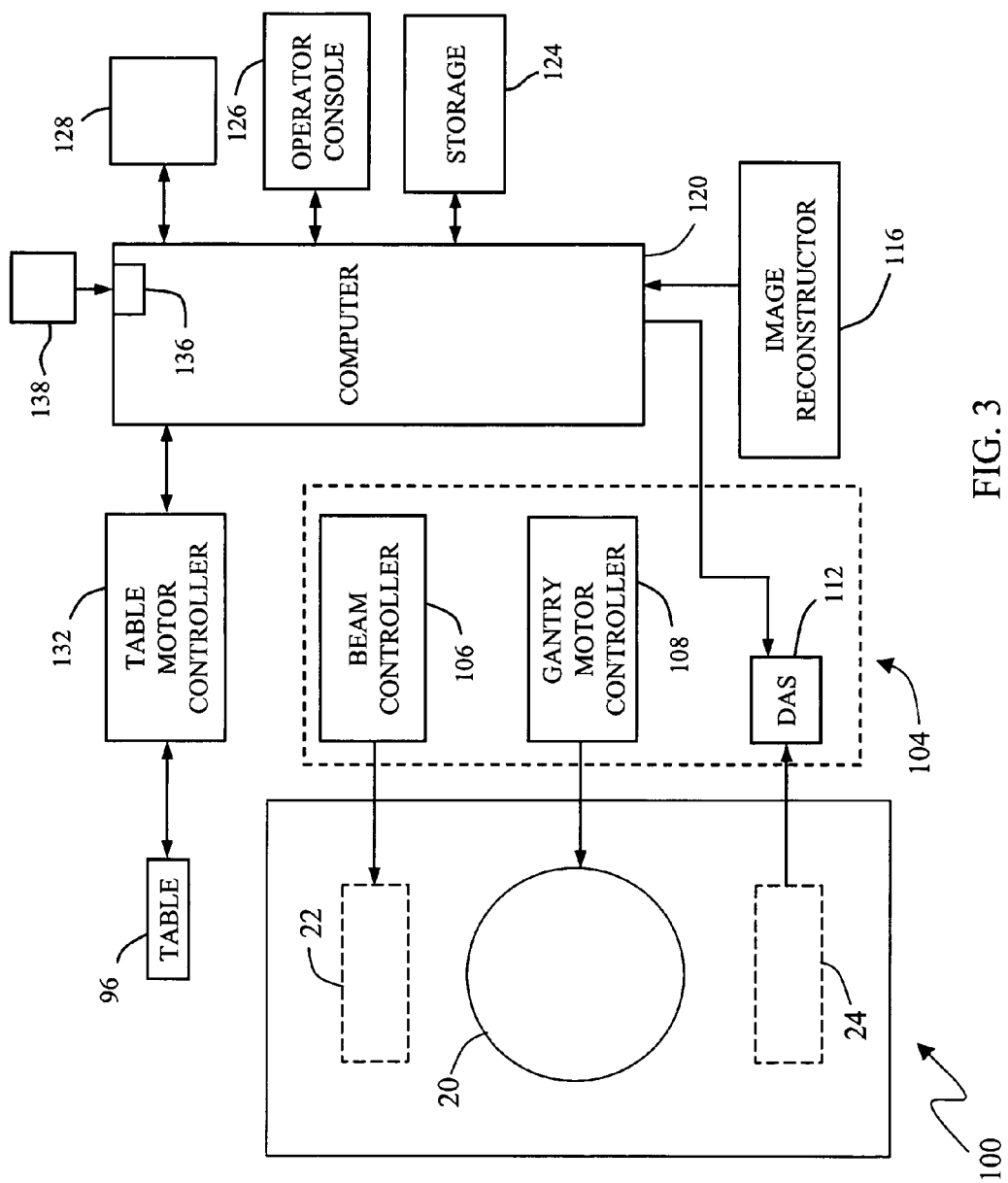
FIG. 3 shows an embodiment of a system, which includes the gantry of FIG. 1, for generating images by using monochromatic x-rays.

FIG. 3 shows an embodiment of a modified computed tomography system 100 for generating images by using. Rotation of gantry 20, operation of gun 42, and operation of laser sources 60 and 62 are governed by a control mechanism 104 of CT system 100. Control mechanism 104 includes a beam controller 106 that provides power and timing signals to gun 42 and laser source 60, and a gantry motor controller 108 that controls a rotational speed and position of gantry 20. A data acquisition system (DAS) 112 in control mechanism 104 samples analog data, such as the attenuation measurements, from detector elements 74 and converts the data to digital signals for subsequent processing. In one embodiment, detector elements 74 are energy discriminating if source 22 generates one or more x-ray beams with multiple energies. In an alternative embodiment, detector elements 74 are non-energy discriminating if source 22 generates a single energy x-ray beam.

An image reconstructor 116 receives sampled and digitized x-ray data from DAS 112 and performs high-speed image reconstruction to generate at least one reconstructed image. In one embodiment, a first reconstructed image is generated from x-ray data containing information produced from attenuation of the first x-ray beam and a second reconstructed image is produced from attenuation of the second x-ray beam. When the first and second x-ray beams are generated consecutively, the first and second images are reconstructed sequentially. When the first and second x-ray beams are generated simultaneously, the first and second images are reconstructed simultaneously. The first and the second reconstructed images can be combined to generate a stereoscopic image. When at least one reconstructed image is applied as an input to a computer 120, computer 120 stores the image in a storage device 124.

Computer 120 also receives commands and scanning parameters from an operator via console 126 that has a keyboard. An associated cathode ray tube display 128 allows the operator to observe at least one reconstructed image and other data from computer 120. The operator supplied commands and parameters are used by computer 120 to provide control signals and information to DAS 112, beam controller 106 and gantry motor controller 108. In addition, computer 120 operates a table motor controller 132 which controls table 96 to position object 92 in gantry 20. Particularly, table 96 moves object 92 through gantry opening 26.

In one embodiment, computer 120 includes a device 136, for example, a floppy disk drive, CD-ROM drive, DVD drive, magnetic optical disk (MOD) device, or any other digital device including a network connecting device such as an Ethernet device for reading instructions and/or data from a computer-readable medium 138, such as a floppy disk, a CD-ROM, a DVD or an other digital source such as a network or the Internet, as well as yet to be developed digital means. In another embodiment, computer 120 executes instructions stored in firmware (not shown). Computer 120 is programmed to perform functions described herein, and as used herein, the term computer is not limited to just those integrated circuits referred to in the art as computers, but broadly refers to processors, microcontrollers, microcomputers, programmable logic controllers, application specific integrated circuits, and other programmable circuits, and these terms are used interchangeably herein.

Additionally, although the herein described systems and methods for generating images by using monochromatic x-rays are described in a medical setting, it is contemplated that the benefits of the systems and methods accrue to non-medical imaging systems such as those systems typically employed in an industrial setting or a transportation setting, such as, for example, but not limited to, a baggage scanning system for an airport, other transportation centers, government buildings, office buildings, and the like. The baggage scanning system is used to scan items, such as, chemical, weapons, drugs, and explosives. The benefits also accrue to micro computed tomography (CT) systems which are sized to study lab animals as opposed to humans.

Technical effects of the herein described systems and methods for generating images by using monochromatic x-rays include enabling pinpointing of a treatment region accurately without a need for registration a separate computed tomography (CT) system having an x-ray source. Images generated by using the herein described systems and methods have good image quality and contrast. Further effects of the herein described systems include therapy of diseases, such as cancer or diseases close to the skin of the subject. The herein described systems and methods provide a possibility of reducing the length of accelerator 44 while accelerating electrons to tens of MeV or alternatively, generating a higher amount of energy than tens of MeV while maintaining the length of accelerator 44.

While the invention has been described in terms of various specific embodiments, those skilled in the art will recognize that the invention can be practiced with modification within the spirit and scope of the claims.

What is claimed is:

1. A system for generating images by using monochromatic x-rays, said system comprising:
    an accelerator configured to increase energy of an electron beam;
    at least one detector element configured to receive x-rays having multiple energies generated by interaction of the electron beam with at least two laser beams, and one of the at least two laser beams has a wavelength that is different than a wavelength of remaining of the at least two laser beams; and
    an image reconstructor configured to reconstruct at least one image by processing the x-rays.

2. A system for generating images in accordance with claim 1 wherein the multiple energies are generated by one of:
    changing a wavelength of one of the at least two laser beams; and
    changing energy of the electron beam.

3. A system for generating images in accordance with claim 1 wherein one of the at least two laser beams interacts with the electron beam and then remaining one of the at least two laser beams interacts with the electron beam.

4. A system for generating images in accordance with claim 1 wherein the x-rays have an energy ranging from ten to two-hundred kilo electron volts.

5. A system for generating images in accordance with claim 1 wherein said accelerator and said at least one detector element are mounted within a gantry that is configured to rotate around an object, wherein said gantry rotates to penetrate the x-rays through the object at varying angles, said at least one detector element is configured to receive at least one attenuated radiation beam as said gantry rotates around the object, and said image reconstructor is configured to reconstruct the image by processing information within the attenuated radiation beam.

6. A system for generating images in accordance with claim 1 wherein one of the at least two laser beams are directed toward the electron beam at an angle ranging from zero degrees to ninety degrees.

7. A system for generating images in accordance with claim 1 wherein said at least one detector element is configured to distinguish between the multiple energies of the x-rays.

8. A system for generating images by using monochromatic x-rays, said system comprising:
   an accelerator configured to accelerate an electron beam received from a gun; and at least one detector element configured to receive x-rays generated by interaction of the electron beam with at least two laser beams, wherein one of the at least two laser beams has a different wavelength than a wavelength of remaining of the at least two laser beams; and
   an image reconstructor configured to reconstruct at least one image by processing the x-rays.

9. A system for generating images in accordance with claim 8 wherein the electron beam simultaneously interacts with the at least two laser beams.

10. A system for generating images in accordance with claim 8 wherein one of the at least two laser beams interacts with the electron beam and then remaining one of the at least two laser beams interacts with the electron beam.

11. A system for generating images in accordance with claim 8 wherein one of the at least two laser beams has an energy that is different than energies of remaining of the at least two laser beams.

12. A system for generating images in accordance with claim 8 wherein the x-rays have an energy ranging from ten to two-hundred kilo electron volts.

13. A system for generating images in accordance with claim 8 wherein said accelerator, said gun and said at least one detector element are mounted within a gantry that is configured to rotate around an object, wherein said gantry rotates to penetrate the x-rays through the object at varying angles, and said at least one detector element detector element is configured to receive at least one attenuated radiation beam as said gantry rotates around the object.

14. A system for generating images in accordance with claim 8 wherein one of the at least two laser beams are directed toward the electron beam at an angle ranging from zero degrees to ninety degrees.

15. A system for generating images in accordance with claim 8 wherein said at least one detector element is configured to distinguish between different energies of the x-rays.

16. A method for generating images by using monochromatic x-rays, said method comprising:
   accelerating an electron beam;
   generating x-rays having multiple energies by interaction of the electron beam with at least two laser beams, and one of the at least two laser beams has a wavelength that is different than a wavelength of remaining of the at least two laser beams; and
   reconstructing at least one image by processing the x-rays.

17. A method for generating images in accordance with claim 16 further comprising simultaneously interacting the electron beam with the at least two laser beams.

18. A method for generating images in accordance with claim 16 further comprising interacting one of the at least two laser beams with the electron beam before interacting remaining one of the at least two laser beams with the electron beam.

19. A method for generating images in accordance with claim 16 further comprising directing one of the at least two laser beams toward the electron beam at an angle ranging from zero degrees to ninety degrees.

* * * * *